United States Patent [19]

Maslyansky et al.

[11] 4,162,214
[45] Jul. 24, 1979

[54] METHOD OF PREPARING BENZENE AND XYLENES

[76] Inventors: Gdal N. Maslyansky, Moskovsk prospekt, 189, kv. 64; Georgy L. Rabinovich, ulitsa Antonova-Ovseenko, 19, korpus 2, kv. 104; Leonid M. Treiger, Moskovsky prospekt, 189, kv. 64; Boris K. Gokhman, ulitsa Voinova, 11, kv. 2; Viktor D. Seleznev, prospekt Obukhovskoi oborony, 108, korpus 4, kv. 58, all of, Leningrad, U.S.S.R.

[21] Appl. No.: 839,347

[22] Filed: Oct. 4, 1977

[51] Int. Cl.$^2$ .................. C07C 3/58; C10G 35/06
[52] U.S. Cl. ............................... 585/471; 208/64; 208/92; 208/65; 585/474; 585/475; 585/478; 585/481; 585/489; 585/752; 585/841
[58] Field of Search ................ 208/62, 64, 92, 63, 208/65; 260/672 R, 672 T, 674 A

[56] References Cited

U.S. PATENT DOCUMENTS

| | | | |
|---|---|---|---|
| 3,671,602 | 6/1972 | Inoue et al. | 260/672 T |
| 3,945,913 | 3/1976 | Brennan et al. | 260/672 R |
| 3,957,621 | 5/1976 | Bonacci et al. | 260/674 A |
| 4,070,408 | 1/1978 | Vickers | 260/672 R |
| 4,078,990 | 3/1978 | Brennan et al. | 260/672 T |

*Primary Examiner*—Herbert Levine
*Attorney, Agent, or Firm*—Lackenbach, Lilling & Siegel

[57] ABSTRACT

A method of preparing benzene and xylenes from catalysates of reforming of gasoline fractions comprising a mixture of aromatic $C_6$–$C_{10}$ hydrocarbons and non-aromatic hydrocarbons which involves separation of a low-boiling fraction boiling out at a temperature of 90°–108° C. from a reforming catalysate by rectification. The remaining high-boiling fraction is processed in the presence of a hydrogen-containing gas at a temperature within the range of from 450° to 600° C. under a pressure of from 10 to 60 atm on a catalyst. The catalyst consists of 1 to 85% by weight of H-mordenite, 0.1 to 10% by weight of a hydrogenating component as which use might be made of oxides of metals of Group VI of the periodic system, sulphides of these metals, metals of Group VIII of the periodic system, sulphides thereof; the balance being a binder. As a result, a liquid product is formed comprising a mixture of aromatic hydrocarbons which is separated by rectification to give benzene, toluene, total xylenes, a mixture of aromatic $C_9$–$C_{10}$ hydrocarbons; at least one of the following streams of hydrocarbons prepared by rectification of the liquid product is recycled back to the stage of processing of a high-boiling fraction: toluene, toluene along with a portion of hydrocarbons boiling out at a temperature exceeding the boiling point of toluene.

The method according to the present invention makes it possible to increase the benzene yield by 3 to 4 times and the yield of xylenes by 1.2–2 times as compared to the content thereof in the reforming catalysate. The method also enables a substantial simplification in the isolation of the desired products.

14 Claims, No Drawings

METHOD OF PREPARING BENZENE AND XYLENES

The present invention relates to methods of preparing aromatic hydrocarbons and, more specifically, benzene and xylenes.

Said aromatic hydrocarbons are extensively used in different branches of industry. Benzene and xylenes comprise the most valuable aromatic hydrocarbons. Benzene is widely used for the manufacture of a great variety of intermediate products such as cyclohexane, ethylbenzene, cumene and the like which are, in turn, useful in the production of synthetic materials, fibers, resins, and rubbers. Among xylenes the most utilizable are p- and o-isomers of xylene employed for the production of terephthalic acid, phthalic anhydride and, therefrom, polyester fibers, resins, varnishes, and plastifying agents.

Aromatic hydrocarbons are prepared mainly by way of catalytic reforming of gasoline fractions on alumino-platinum catalysts. The reforming catalysates comprise a mixture of aromatic and non-aromatic, predominantly paraffin, hydrocarbons. Aromatic hydrocarbons cannot be recovered from the reforming catalysates by a conventional rectification, since they form azeotropic mixtures with non-aromatic hydrocarbons. Therefore, preparation of aromatic hydrocarbons from reforming catalysates is performed by way of extraction thereof with selective solvents such as diethylene and triethylene glycols, furfurol, sulpholane and the like. To prepare benzene and toluene, a fraction of a straight-run gasoline of 60°–105° C. is subjected to catalytic reforming. To prepare simultaneously benzene, toluene and xylenes subjected to reforming is a fraction of 60°–140° C. To prepare mainly xylenes subjected to reforming is a fraction of 105°–140° C. If a wider fraction is subjected to reforming such as 60°–180° C., then besides benzene, toluene and xylenes there is formed a great number of other aromatic $C_9$–$C_{10}$ hydrocarbons.

The modern bi- and poly-metallic reforming catalysts enable the production of catalysates containing 60 to 80% by weight of aromatic hydrocarbons. Such are the yields of aromatic compounds in the reforming of wide fractions 60°–180° C., 85°–180° C., 70°–180° C.; resources of these fractions are especially vast and constitute 15 to 20% as calculated for petroleum.

Recovery of aromatic hydrocarbons by extraction from reforming catalysates has the following disadvantages. Upon extraction only such aromatic hydrocarbons are obtained which are present in the reforming catalysate. In reforming catalysates of wide gasoline fractions about 30 to 40% of aromatic hydrocarbons constitute aromatic $C_9$–$C_{10}$ hydrocarbons which are practically non-utilized in the organic synthesis, about 20 to 25% is the share of toluene which also has a quite limited application. At the same time, content of benzene in reforming catalysates of wide fractions accounts for only 1 to 6% by weight. Therefore, the content of most valuable aromatic hydrocarbons, i.e. benzene and aromatic $C_8$ (total xylenes) is, as a rule, below 50% by weight of the total amount of aromatic hydrocarbons.

For the reasons discussed hereinabove, to increase the yield of most valuable products, the extracted aromatic hydrocarbons are treated in additional processes. Toluene is hydrodealkylated to benzene according to the reaction:

$$C_6H_5CH_3 + H_2 \rightarrow C_6H_6 + CH_4$$

or disproportionated to benzene and xylenes:

$$2C_6H_5CH_3 \rightarrow C_6H_4(CH_3)_2 + C_6H_6$$

To obtain the maximum possible yield of xylene, toluene and aromatic $C_9$ hydrocarbons are transalkylated to xylenes:

$$C_6H_5CH_3 + C_6H_3(CH_3)_3 \rightarrow 2C_6H_4(CH_3)_2$$

Most valuable isomers of xylenes are p- and o-xylenes. To increase the yield thereof, less valuable aromatic $C_8$ hydrocarbons (m-xylene and ethylbenzene) are isomerized to p- and o-xylenes.

Therefore, the prior art method of preparing benzene and xylenes (including p- and o-xylenes) from reforming catalysates of wide fractions comprises extraction of aromatic hydrocarbons and subsequent performance of a series of processes such as dealkylation, disproportionation, transalkylation, and isomerization.

Known in the art is another method of preparing pure aromatic hydrocarbons from aromatized gasolines by means of processes of hydrocracking-hydrodelakylation, wherein non-aromatic hydrocarbons are hydrocracked to gaseous products, while alkylaromatic hydrocarbons are dealkylated to benzene which is recovered by rectification. These processes are usually performed with or without catalysts at a temperature within the range of from 500° to 800° C.

The method of hydrocracking-hydrodealkylation is used mainly for processing of pyrolysis gasolines containing small amounts of non-aromatic hydrocarbons (10 to 25% by weight) and the content of benzene is higher than that of homologues thereof. Utilization of this process for the treatment of reforming catalysates is poorly efficient due to the unfavorable composition of the aromatic hydrocarbons in this feedstock. As it has been mentioned hereinbefore, more than 30% by weight of aromatic hydrocarbons in a reforming catalysate are represented by aromatic $C_9$–$C_{10}$ hydrocarbons and dealkylation thereof to benzene is accompanied by substantial losses of the liquid product and, accordingly, by a high consumption rate of hydrogen as it can be seen from the stoichiometric character of the reaction:

$$C_6H_3(CH_3)_3 + 3H_2 \rightarrow C_6H_6 + 3CH_4$$

Even upon a selective performance of the process, dealkylation of aromatic $C_9$–$C_{10}$ hydrocarbons proceeds so that about 35 to 40% by weight of the feedstock is converted to a gas. The total xylenes (aromatic $C_8$ hydrocarbons) present in the feedstock are converted to benzene also with a substantial weight loss (27%). At the same time, xylenes are not less valuable than benzene.

Hydrocracking of paraffin hydrocarbons present in the feedstock also necessitates a high consumption rate of hydrogen, as it can be seen from the stoichiometric character of the reaction:

$$C_7H_{16} + 6H_2 \rightarrow 7CH_4$$

All these drawbacks results in great losses of the liquid product, considerable gas-formation and high consumption of hydrogen. Thus, upon hydrodealkylation of a reforming catalysate of a wide fraction on a catalyst containing Pt, Pd, Cr$_2$O$_3$ supported by Al$_2$O$_3$ more than half of the starting feedstock is converted to gas and hydrogen consumption is about 10% of the total amount of the feedstock.

The above-mentioned disadvantages are responsible for the fact that reforming catalysates of wide fractions do not find any commercial implementation as a starting feed for the processes of hydrodealkylation-hydrocracking.

Known in the art is still another method of preparing aromatic hydrocarbons, wherein from the reforming catalysates there are simultaneously obtained an aromatic concentrate and isobutane. According to this method, reforming of gasoline is effected under mild conditions, whereunder the aromatic hydrocarbons are formed mainly from naphthenic hydrocarbons, whereas dehydrocyclization of paraffins to aromatic hydrocarbons constitutes below 40%. In accordance with this method, the reforming catalysate or a portion thereof after separation of C$_5$–C$_6$ hydrocarbons by distillation is fed to the hydrocracking zone. The hydrocracking is performed at a temperature within the range of from 340° to 450° C. under a pressure of from 10 to 70 atm using a catalyst containing mordenite combined with alumina, Pd and Ni components preferably in the form of sulphides. Space velocity of the feed supply is varied within the range of from 1.0 to 10 volumes per one volume of the catalyst per hour; circulation rate of hydrogen is 3,000 to 20,000 sft$^3$/barrel.

Under the above-described conditions, paraffin hydrocarbons contained in the reforming catalysate are subjected to hydrocracking with the formation of paraffin C$_2$–C$_4$ hydrocarbons, mainly isobutane, and simultaneously obtained is a concentrate of aromatic hydrocarbons contained in the starting feedstock, with a small amount of paraffin hydrocarbons. Paraffins C$_5$–C$_6$ are distilled from the liquid product and then isomerized in the presence of hydrogen by a separate process of isomerization. The propane-butane fraction of the product is dehydrogenated in a separate process to give olefins which are then employed for alkylation of isobutane.

This method of preparing aromatic hydrocarbons has certain disadvantages.

First of all, the aromatic concentrate formed in the process contains mainly those aromatic hydrocarbons C$_6$–C$_{10}$ which are present in the reforming catalysate at the same non-favorable ratio therebetween, i.e. a low content of benzene and a high content of low-value aromatic hydrocarbons: toluene and C$_9$–C$_{10}$ aromatics.

Secondly, under the process conditions an exhaustive hydrocracking of non-aromatic hydrocarbons is not achieved, whereby separation of pure aromatic hydrocarbons by rectification of the resulting aromatic concentrate is impossible. In particular, it is impossible to recover total xylenes of a required purity grade by rectification of said aromatic concentrate. For this reason, the resulting concentrate of aromatic hydrocarbons is considered as a high-octane component of an automobile gasoline.

It is an object of the present invention to provide such a method of preparing benzene and xylenes which would make it possible to substantially increase the yield of said products and to simplify their separation.

It is another object of the present invention to obtain total xylenes substantially free from ethylbenzene thus facilitating a further treatment and separation of xylenes.

Still another object of the present invention is to overcome the necessity of performing a separate process for isomerization of xylenes.

These and other objects of the present invention are accomplished by a method of preparing benzene and xylenes from reforming catalysates of gasoline fractions comprising mixtures of aromatic C$_6$–C$_{10}$ hydrocarbons and non-aromatic hydrocarbons, wherein a low-boiling fraction is distilled from the reforming catalysate and the remaining high-boiling fraction is treated in the presence of hydrogen at an elevated temperature and under a pressure within the range of from 10 to 60 atm on a catalyst consisting of mordenite, a hydrogenating agent, the balance being a binder. In accordance with the present invention, a low-boiling fraction, boiling out to a temperature of from 90° to 108° C., is separated by distillation, the remaining high-boiling fraction is treated at a temperature of from 450° to 600° C., using a catalyst consisting of H-mordenite in an amount of from 1 to 85% by weight, MoO$_3$, WO$_3$, Co, Pt taken either separately or in various combinations with each other in an amount of from 0.1 to 10% by weight as a hydrogenating agent. The resulting liquid product is separated by rectification to give benzene, toluene, total xylenes and a mixture of C$_9$–C$_{10}$ aromatic hydrocarbons. Recycled back to the stage of treatment of the high-boiling fraction are hydrocarbons prepared by rectification of the liquid product: toluene or toluene along with a portion of hydrocarbons boiling above the boiling point of toluene.

As the reforming catalysates use is made of catalysates of reforming of wide gasoline fractions containing a mixture of aromatic C$_6$–C$_{10}$ hydrocarbons and non-aromatic hydrocarbons. Such catalysates are obtained upon a catalytic reforming of fractions of straight-run gasoline boiling out within the range of from 60° to 180° C., for example fractions over 85° to 180° C., 70° to 160° C., 70° to 180° C. and the like. It is preferable that the content of aromatic hydrocarbons in said catalysates be above 60% by weight. The latter are obtained upon reforming gasolines under severe conditions using aluminoplatinum catalysts containing additives of rhenium, iridium and other promotors. Severe reforming conditions mean a relatively low pressure and elevated temperatures, at which the process of reforming to produce highly-aromitized gasolines is performed.

In accordance with the method of the present invention, a low-boiling (head) fraction with the boiling end between 90° and 108° C., preferably from 100° to 106° C., is previously distilled-off from the starting reforming catalysate. The head fraction constitutes 20 to 35% by weight of the reforming catalysate. It contains mainly paraffin hydrocarbons, benzene and a minor amount of toluene. The remaining high-boiling portion of the reforming catalysate is a starting feedstock for the catalytic stage of the process. It contains toluene, aromatic C$_8$, C$_9$ and possibly C$_{10}$ hydrocarbons as well as non-aromatic (paraffin) hydrocarbons. The amount of paraffin hydrocarbons in said fraction is, as a rule, below 15% by weight. This high-boiling portion of the catalysate along with hydrogen or a hydrogen-containing gas and a recycled stream of a portion of the liquid product obtained in this process is passed, under the above-described conditions, through a catalyst bed consisting of H-mordenite, a hydrogenating component and a binder.

An important feature of the present invention is that the reaction stage is performed at a temperature within the range of from 450° to 600° C. in the catalyst bed. At a temperature below 450° C. the liquid product contains an increased amount of paraffin $C_9$–$C_{10}$ hydrocarbons which hinder separation of xylenes by rectification. At a temperature exceeding the above-indicated upper temperature limit of the process, stability of the catalyst is impaired. As a result, a gas-liquid mixture is obtained which is cooled and the gas stream is separated from the liquid product. The liquid product comprising a mixture of aromatic hydrocarbons is separated by rectification to give benzene, toluene, pure total xylenes and a fraction of aromatic $C_9$–$C_{10}$ hydrocarbons. Toluene is recycled to the reaction zone as it is or along with the fraction of aromatic $C_9$–$C_{10}$ hydrocarbons, or along with a concentrate of m-xylene and the fraction of aromatic $C_9$–$C_{10}$ hydrocarbons. The concentrate of m-xylene is obtained after separation of p- and o-xylenes from the total xylenes by conventional techniques (crystallization, rectification, molecular-sieve absorption). By the term "concentrate of m-xylene" is meant a mixture of aromatic $C_8$ hydrocarbons containing mainly m-xylene and also ethylbenzene and a minor amount of the non-recovered p- and o-xylenes. A portion of toluene obtained in the process may be withdrawn therefrom when required. However, recycle of toluene or at least a portion thereof is an obligatory condition of the process. It is preferable to perform recycling of the total amount of toluene recovered from the liquid product.

The fraction of aromatic $C_9$–$C_{10}$ hydrocarbons separated by rectification contains mainly aromatic $C_9$ hydrocarbons. In all the process embodiments, as the desired products there are discharged benzene and pure total xylenes. Benzene separated from the liquid product of the process usually contains as impurities a certain amount of non-aromatic hydrocarbons. If it is necessary to obtain benzene with a purity over 99.5%, it may be prepared by purification of the separated benzene from said impurities using conventional methods of extractive or azeotropic rectification.

The preferred embodiment of the method according to the present invention contemplates isolation of pure benzene from two streams: from the liquid product of the process and from the low-boiling fraction of the reforming catalysate.

The purity grade of total xylenes recovered from the mixture of aromatic hydrocarbons by rectification is 99.5% and above.

It is known that the content of n-nonane, $C_9$ naphthenes and $C_{10}$ paraffins in total xylenes should not exceed 0.2% by weight. Otherwise, pure o-xylene cannot be recovered by rectification of total xylenes.

The method according to the present invention ensures substantially complete hydrocracking of said impurities. Total xylenes obtained in the process contain practically no $C_{10}$ paraffins, $C_9$ naphthenes and n-nonane. A distinctive feature of the total xylenes as prepared by the method according to the present invention resides is that only an insignificant amount of ethylbenzene (1.5 to 3% by weight) is present therein. The total xylenes contain about 50% by weight of m-xylene and about 23 to 26% by weight of each of o-xylene and p-xylene.

The catalytic stage of the process is performed at a space velocity of the starting feedstock along with the recycle of from 1 to 8 volumes per volume of the catalyst per hour.

The ratio between a hydrogen-containing gas and the mixture of feedstock with recycle is varied from 600 to 2,000 nl/l.

The hydrogen-containing gas, as a rule, is recycled in the process to maintain the concentration of hydrogen therein of at least 50% by volume. The required concentration is ensured for example by adding an appropriate amount of fresh hydrogen. The gaseous products consist of paraffin $C_1$–$C_4$ hydrocarbons; therewith, the yield of $C_2$–$C_4$ hydrocarbons is as high as 8–10 times of the yield of methane.

The catalyst employed in the method according to the present invention consists of 1 to 85% by weight of n-mordenite, 0.1 to 10% by weight of hydrogenating agent, the balance being constituted by a binder.

H-mordenite is a crystalline alumosilicate of a cubic structure having an inlet port diameter of from 6 to 10 Å and a molar ratio of $SiO_2/Al_2O_3$ of 10 and over, generally of from 10 to 30.

The above-indicated wide range of mordenite content in the catalyst is explained by different activity thereof depending on a molar ratio of $SiO_2/Al_2O_3$. Thus, common H-mordenite having a molar ratio of 10 to 12 is substantially less active as compared to a dealuminated mordenite having a high value of the molar ratio of $SiO_2/Al_2O_3$. For this reason, common mordenite should be contained in the catalyst in a greater amount that the dealuminated one. Increasing the content of mordenite above the indicated upper limit is inefficient, since it does not result in a higher activity of the catalyst and even lowers its mechanical strength. The content of mordenite below 1% by weight in the catalyst results in a lowered activity thereof in the process below the critical level.

As hydrogenating components in the catalyst according to the present invention use is made of metals pertaining to Group IV and Group VIII of the periodic system, preferably Mo, W, Co, Pt. They may be present in the catalyst in different forms: the Group VI metal—in the oxide form ($MoO_3$, $WO_3$) or sulphide form; Group VIII metals—in the elemental or sulphide form. It is especially advantageous to use Mo per se or in combination with the above-mentioned components.

With a content of the hydrogenating components of from 0.1 to 10% by weight, the Group VIII metals are taken as calculated for the elemental condition, and the Group VI metals—as calculated for trioxide.

When $MoO_3$ is used, its amount in the catalyst might constitute several percent, whereas in the case of platinum the amount of the latter constitutes decimal fractions of a percent.

The catalyst composition might include H-Me-mordenite, wherein Me is at least one element selected from the group consisting of rare-earth and alkali-earth metals such as Ca, Mg, Ce, La, and commercial mixtures of lanthanides.

Said elements are introduced into the mordenite structure using ion-exchange methods; in doing so, the maximal amount of the elements should not exceed 50% of the theoretically possible degree of substitution of hydrogen cations in n-mordenite.

The binder (matrix) comprises a material imparting a required mechanical strength to the catalyst. As the binder use might be made of amorphous alumosilicate, silica gel, alumina. It is preferable to employ alumina as the binder.

The method according to the present invention ensures an exhaustive hydrocracking of paraffin hydrocarbons forming azeotropic mixtures with aromatic hydrocarbons, whereby separation of benzene and xylenes becomes simplified. A complex combination of chemical reactions of transformation of aromatic hydrocarbons results, in the final end, in their complete conversion to valuable products, i.e. benzene and xylenes. The method according to the present invention has made it possible to balance a great number of reaction (dealkylation, disproportionation, transalkylation, isomerization of aromatic hydrocarbons; hydrocracking of non-aromatic hydrocarbons) and to inhibit undesirable reactions of decomposition of the aromatic ring.

The method according to the present invention makes it possible to increase the yield of benzene by 3–4 times; that of xylenes—by 1.2 to 2 times as compared to the content of these hydrocarbons in the reforming catalysate. Separation of said products is also substantially simplified.

Total xylenes prepared by the method according to the present invention have a higher quality than those obtained from catalytic reforming and extraction. They contain an insignificant amount (1 to 3% by weight) of ethylbenzene and, hence, a greater amount of xylenes thus facilitating their subsequent separation and isomerization.

Furthermore, one of the embodiments of the method according to the present invention does not require any additional unit for isomerization of m-xylene, since after separation of p- and o-xylenes, m-xylene might be recycled back into the process.

Therefore, the method according to the present invention makes it possible to simultaneously solve a series of different problems which hitherto have been solved through the use of a whole number of individual processes (extraction, dealkylation, disproportionation, transalkylation, isomerization of aromatic hydrocarbons).

An important feature of the method according to the present invention is that it enables avoiding separated reforming of narrow and wide gasoline fractions in order to produce aromatic hydrocarbons and a high-octane component and makes it possible to obtain both types of products at a single high-capacity plant of catalytic reforming so that a portion of the catalyst employed at this plant could be treated according to the method of the present invention.

The method according to the present invention is technologically simple and can be performed in the following manner.

A reforming catalysate is fed into a rectification column, wherein the low-boiling portion of the catalysate is distilled-off. The high-boiling portion of the catalysate serving as a starting feedstock for the catalytic stage of the process is discharged from the column bottom. In some cases, where a reforming catalysate contains, besides aromatic $C_6$–$C_{10}$ hydrocarbons, also aromatic $C_{11}{}^+$ hydrocarbons, it is advisable to additionally separate the high-boiling fraction from a heavy residue containing mainly aromatic $C_{11}{}^+$ hydrocarbons which causes coking of the catalyst. In this case the high-boiling fraction is fed into a second column, wherein it is distilled and discharged from the column top, whereas the heavy residue is withdrawn from the bottom. The high-boiling fraction of the catalysate containing aromatic $C_7$–$C_{10}$ hydrocarbons is further delivered into the reaction unit of the process.

The process according to the present invention is exothermal. It is effected in a reactor unit consisting of a number of series-connected reactors or in a shelf-type reactor, wherein the catalyst is placed on a number of shelves. In between the reactors or shelves the reaction mixture is cooled by removing excessive heat by admission of cold hydrogen and/or a portion of the feedstock. The feedstock for the catalytic stage and a portion of the liquid product of the process to be recycled are evaporated in heat-exchangers, mixed with the recycled hydrogen-containing gas and fresh hydrogen-containing gas (generally it is the hydrogen-containing gas from the catalytic reforming process).

The mixture is heated in a furnace to a required temperature. The heated mixture is passed through a cascade of series-mounted reactors or a shelf-type reactor. At the outlet the mixture is cooled in heat-exchangers, condensed and delivered to a gas-separator unit, wherein the gaseous phase is separated from the liquid one. The gaseous phase contains hydrogen and gaseous hydrocarbons. To reduce the supply rate of fresh hydrogen, the recycled hydrogen-containing gas is usually purified from the gaseous hydrocarbons by means of absorption. The liquid product of the process is further delivered from the gas-separator unit into a stabilization column, wherein dissolved light hydrocarbons $C_1$–$C_4$ are separated from the liquid product. The stable liquid product is then passed into a number of rectification columns, wherein successively separated are: benzene fraction, toluene, total xylenes and aromatic $C_9$–$C_{10}$ hydrocarbons. Toluene is recycled into the process, either separately or along with aromatic $C_9$–$C_{10}$ hydrocarbons. In the case, where a concentrate of m-xylene is recycled along with toluene and aromatic $C_9$–$C_{10}$ hydrocarbons, p- and o-xylenes are previously separated by conventional methods from total xylenes in special units. O-xylene is usually recovered by rectification and p-xylene—by crystallization or molecular-sieve adsorption. The m-xylene concentrate remaining after separation of p- and o-xylenes contains a certain amount of ethylbenzene and non-removed portion of p- and o-xylenes.

Pure benzene from the benzene fraction produced in the process is obtained by conventional methods of azeotropic or extractive distillation.

In the azeotropic distillation, as the azeotrope-forming agent use is generally made of acetone; in the extractive distillation of benzene use is made of conventional solvents such as N-methylpyrrolidone, N-formylmorpholine and the like.

If the reforming catalysate employed in the process contains a substantial amount of benzene which is present in the low-boiling fraction, it is economically efficient to recover pure benzene from that fraction as well. As an embodiment of benzene isolation in this case there might be intermixing of the benzene fraction from the process with the low-boiling fraction of the reforming catalysate and subsequent recovery of pure benzene from this mixture by means of extraction with selective solvents. As selective solvents for the extraction glycols, sulpholane, N-methylpyrrolidone and the like might be used.

The total xylenes produced by rectification of the liquid product are sufficiently pure and can be used in other processes without any additional purification.

The catalyst for the process is prepared in a conventional manner characteristic of the preparation of zeolite catalysts with a binder. The starting Na-mordenite is converted to the H-form by treating same with an acid such as hydrochloric acid. Another method contemplates treatment of Na-mordenite with solutions of ammonium salts such as ammonium chloride. In this case, NH4-mordenite is formed which is converted to H-mordenite upon calcination. The catalyst is prepared by intermixing a paste of aluminum hydroxide with a finely-divided powder of H-mordenite or NH4-mordenite and with a solution of a compound of the hydrogenating component such as ammonium molybdate. After the production of a uniform plastic mass, the latter is moulded by extrusion; the resulting extrudates are dried at a temperature within the range of from 50° to 130° C. and calcined in the air current.

The hydrogenating component can be also introduced by impregnating the calcined composition of H-mordenite and a binder.

When use is made of H-Me-mordenite, then alkali-earth and rare-earth metals are incorporated by way of ion-exchange. Usually NH4-mordenite is employed for such ion-exchange.

Another method of preparation of the catalyst might reside in the introduction of mordenite into a hydrosol alumina followed by the formation of gel beads in an oil medium. Generally, the catalyst might have the form of extrudates, tablets, beads, or irregular-shape granules.

To reduce the excessive activity, the calcined catalyst is treated, as a rule, with sulphur or sulphur compounds (hydrogen sulphide, sulphur-organic compounds) in a stream of hydrogen or in a stream of hydrogen and the feedstock at a temperature within the range of from 300° to 450° C.

For a better understanding of the present invention some specific Examples are given hereinbelow by way of illustration.

EXAMPLE 1

A catalysate of reforming of a fraction of straight-run gasoline containing 72% of aromatic $C_6$–$C_{10}$ hydrocarbons is separated, by rectification, into a low-boiling fraction with the boiling end of 105° C. and a high-boiling (bottoms) fraction.

The yields of the low-boiling and high-boiling fractions are 28 and 72% by weight respectively as calculated for the reforming catalysate.

The low-boiling fraction has the following composition, percent by weight:

| | |
|---|---|
| non-aromatic hydrocarbons | 77.0 |
| benzene | 19.3 |
| toluene | 3.7. |

The high-boiling fraction has the following composition, percent by weight:

| | |
|---|---|
| non-aromatic hydrocarbons | 8.9 |
| toluene | 22.6 |
| $C_8$-aromatics | 34.8 |
| $C_9$-aromatics | 30.5 |
| $C_{10}$-aromatics | 3.2. |

As the starting feedstock for the reaction stage use is made of the high-boiling stage of the reforming catalysate. The experiment is conducted using a catalyst of the following composition, percent by weight: $MoO_3$ 6.9; H-mordenite ($SiO_2/Al_2O_3$=12) 69.8; alumina 23.3. The catalyst extrudates have the following dimensions: length 4 mm, diameter 3 mm. Bulk weight is 0.5 g/cm$^3$. The experiment is conducted in a direct-flow apparatus with circulation of a hydrogen-containing gas. Temperature in the catalyst bed is varied within the range of from 500° to 510° C., pressure is 35 atm, space rate of the feed supply (along with the recycle) is 2 hr$^{-1}$; circulation ratio of the gas is 1,800 nl/l of the feed and recycle; supply rate of fresh hydrogen is 200 nl/l of the feed and recycle. Content of hydrogen in the circulated gas is 75% by volume.

The catalyst is previously sulphidized with dimethyl-sulphide by adding same to the starting feedstock at a temperature of from 380° to 400° C. under the pressure of 35 atm, whereafter the temperature is brought to 500°–510° C.

Toluene is added to the fresh feedstock until the yield of toluene, as calculated for the starting feed, becomes equal to the amount of toluene added to the fresh feedstock. Such stationary conditions of the process are achieved at the ratio of the fresh feedstock to the recycled toluene of 0.63 and 0.37 part by weight respectively, where the total is assumed to be equal to 1. Under these conditions, the yield of liquid product $C_5^+$ as calculated for the mixture of fresh feedstock with the recycle, is 88.0% by weight, including: benzene 13.0, toluene 37.0, xylene 29.2; $C_9$–$C_{10}$-aromatics 7.8; $C_5$–$C_9$ non-aromatics 1.0. The content of non-aromatic $C_9$ hydrocarbons in the liquid products is 0.1% by weight, including n-nonane 0.02% by weight.

The gaseous products have the following composition, percent by weight:

| | |
|---|---|
| hydrogen | 9.3 |
| methane | 9.2 |
| ethane | 57.1 |
| propane | 17.9 |
| butanes | 6.5. |

Benzene with a purity of 95.5% is isolated by rectification of the catalysate along with toluene, total xylenes, and a fraction boiling above the boiling point of toluene ($C_9$–$C_{10}$ aromatic hydrocarbons). Continuously supplying toluene, as a recycle, to the catalytic zone, there are produced (as calculated for 100% of a fresh high-boiling fraction of the catalysate):

| | |
|---|---|
| benzene 21.5% (20.5% calculated for pure benzene); | |
| total xylenes | 46.4% |
| $C_9$–$C_{10}$-aromatics | 12.5. |

The total xylenes recovered by rectification from the liquid products of the process have a purity of 99.6% by weight and the following isomeric composition, percent by weight:

| | |
|---|---|
| ethylbenzene | 2.0 |
| p-xylene | 22.0 |
| o-xylene | 26.4 |
| m-xylene | 49.6. |

These results remain practically unchanged during 400 hours of the catalyst operation.

Benzene formed in the process is mixed with the low-boiling fraction of the reforming catalysate and pure benzene is isolated from the mixture by extraction with a selective solvent (diethylene glycol). There are obtained, as calculated for the starting reforming catalysate, 19.8% by weight of benzene and 33.3% by weight of total xylenes.

EXAMPLE 2

Process conditions, catalyst and composition of the starting stock are the same as in the foregoing Example 1. Recycled is toluene along with aromatic $C_9$–$C_{10}$ hydrocarbons. Experimentally found ratio of the fresh feedstock and recycle at the reactor inlet is:

| | |
|---|---|
| fresh feedstock | 0.55 |
| toluene | 0.315 |
| $C_9$–$C_{10}$-aromatics | 0.135 |
| Total: | 1.0 |

The yield of the liquid product, as calculated for the mixture of the feedstock and recycle, is 88.0% by weight including: benzene 9.5; toluene 31.5; total xylene 32.8; $C_9$–$C_{10}$-aromatics 13.5; $C_5$–$C_9$ non-aromatics 0.7. The content of non-aromatic $C_9$ compounds is 0.1% including n-nonane 0.02%.

The gaseous products have the following composition, percent by weight:

| | |
|---|---|
| hydrogen | 8.4 |
| methane | 9.5 |
| ethane | 59.4 |
| propane | 16.3 |
| butane | 6.4 |

The liquid product is separated by rectification to: benzene, toluene, total xylenes, aromatic $C_9$–$C_{10}$ hydrocarbons. Toluene and a fraction boiling at a temperature above the boiling point of xylenes is recycled to the process in the above-mentioned ratio to the fresh feedstock. The yield of benzene and total xylenes, as calculated for the fresh feedstock (high-boiling fraction of the reforming catalysate), is 17.3 and 59.6% by weight respectively.

The total xylenes have the following composition, percent by weight:

| | |
|---|---|
| ethylbenzene | 1.6 |
| p-xylene | 22.6 |
| o-xylene | 25.4 |
| m-xylene | 50.4 |

Taking into account separation of benzene from the head fraction of the reforming catalysate, the yield of benzene is 17.8% by weight and that of total xylenes is 42.8% by weight as calculated for 100% of the catalysate.

EXAMPLE 3

Use is made of a catalysate of reforming of a straight-run gasoline (85°–180° C.), wherefrom a light fraction is previously distilled boiling-out up to 103° C. The high-boiling fraction has the following hydrocarbon composition, percent by weight:

| | |
|---|---|
| non-aromatic hydrocarbons | 9.2 |
| toluene | 27.3 |
| $C_8$-aromatics | 46.0 |
| $C_9$-aromatics | 15.6 |
| $C_{10}$-aromatics | 1.9 |

The catalyst is employed containing, percent by weight: $MoO_3$, 5.0; Co, 1.0; H-mordenite, 47; alumina, 47. Conditions are the same as in Example 1 hereinbefore, except that the space velocity of supply of the feedstock and recycle is 3 hr$^{-1}$ and the content of hydrogen in the recycled gas is 7% by volume. Recycled in combination are toluene, m-xylene (with the impurity of ethylbenzene) and the fraction of aromatic hydrocarbons boiling at a temperature above the boiling point of xylenes. Experimentally found ratio between the fresh feedstock and recycle is:

| | |
|---|---|
| fresh feedstock | 0.33 |
| toluene | 0.33 |
| m-xylene | 0.18 (0.17 m-xylene and 0.01 ethylbenzene |
| $C_9$–$C_{10}$-aromatics | 0.16 |
| Total: | 1.0 |

The yield of liquid product $C_5^+$, as calculated for the passed mixture, is 93.2% by weight including:

| | |
|---|---|
| benzene | 7.4 |
| toluene | 33.0 |
| o-xylene | 9.5 |
| p-xylene | 8.5 |
| m-xylene with ethylbenzene | 18.0 |
| $C_9$–$C_{10}$-aromatics | 16.0 |
| $C_5$–$C_9$-non-aromatics | 0.8 |

The content of non-aromatic $C_9$ hydrocarbons in the liquid product is 0.08% by weight including 0.01% by weight of n-nonane. With the account of continuous separation of p- and o-xylenes from the total xylenes produced in the process and recycle of toluene along with the concentrate of m-xylene and fraction of aromatic $C_9$–$C_{10}$ hydrocarbons, there are obtained, as calculated for the high-boiling fraction of the reforming catalysate, percent by weight:

| | |
|---|---|
| benzene | 22.4 |
| o-xylene | 28.6 |
| p-xylene | 25.7 |

Example 3 illustrates the possibility of carrying out, under the above-mentioned conditions along with other reactions, the reaction of isomerization of xylenes.

EXAMPLE 4

The starting feedstock, catalyst and process conditions are the same as in the foregoing Example 1, except that the temperature in the catalyst bed is maintained within the range of from 440° to 450° C. The experiment being conducted with the use of a fresh feedstock, the yield of the liquid product is 89% by weight, including: benzene 7.3; toluene 25.7; total xylenes 33.1; $C_9$–$C_{10}$-aromatics 15.8; $C_5$–$C_{10}$-non-aromatics 7.1. The content of non-aromatic $C_9$ hydrocarbons in the catalysate is 0.29% by weight including 0.05% by weight of n-nonane; the content of i-$C_{10}$ is 0.06% by weight. With the above-indicated content of the non-aromatic hydrocarbons separation of pure total xylenes by rectification is rather difficult. The Example illustrates the minimal temperature at which carrying-out the process is still tolerable.

When the process is conducted under the same conditions, except that the catalyst bed temperature is varied within the range of from 590° to 600° C., the catalyst operation is not as stable as required. After only 70 hours of operation the content of $C_9$ paraffin hydrocarbons is about 0.3% by weight, including 0.06% by weight of n-nonane. This example illustrates the upper limit of the process temperature.

EXAMPLE 5

Use is made of a catalysate of reforming of a straight-run gasoline (85°–180° C.) fraction containing 63% by weight of aromatic hydrocarbons. After distilling-off the low-boiling fraction boiling-out up to 102° C., a high-boiling fraction (68.5% by weight of the catalyst) is obtained having the following composition, percent by weight:

| | |
|---|---|
| non-aromatics | 13.5 |
| toluene | 20.5 |
| $C_8$-aromatics | 33.2 |
| $C_9$-aromatics | 29.2 |
| $C_{10}$-aromatics | 3.6. |

Use is made of a catalyst containing, percent by weight: $MoO_3$, 7.5; H-mordenite ($SiO_2/Al_2O_3=20$), 2.5; alumina, 90.0.

An experiment with the high-boiling fraction and recycle of toluene and aromatic $C_9$–$C_{10}$ hydrocarbons is conducted at the temperature of 480° C., space rate of the feedstock and recycle supply of 2 $hr^{-1}$, circulation ratio of the gas of 1,200 nl/l of the feed and recycle and fresh hydrogen supply rate of 300 nl/l of the feed and recycle. The content of hydrogen in the recycled gas is 62% by volume. The mixture of feedstock and recycle at the reactor inlet contains 0.555 part by weight of the fresh feedstock, 0.325 part by weight of toluene and 0.12 part by weight of aromatic $C_9$–$C_{10}$ hydrocarbons, the total being assumed as 1. The yield of liquid $C_5+$ product is 85.4% by weight including: benzene 8.2; toluene 32.5; total xylenes 29.7; aromatic $C_9$–$C_{10}$ hydrocarbons 12.0; non-aromatic $C_5$–$C_9$ hydrocarbons 3.0. The content of non-aromatic $C_9$ hydrocarbons is 0.2% by weight including 0.03% by weight of n-nonane.

EXAMPLE 6

Use is made of a catalyst containing, percent by weight: $MoO_3$ 7.5; H-mordenite (($SiO_2/Al_2O_3=20$) 1; alumina 91.5.

Process conditions, feedstock and proportions of the fresh feedstock, toluene and aromatic $C_9$–$C_{10}$ hydrocarbons at the reactor inlet are the same as in the foregoing Example 5. The liquid product yield is 88.9% by weight including: benzene 7.1; toluene 34.3; xylene 30.2; $C_9$–$C_{10}$ aromatics 13.2; $C_5$–$C_9$ non-aromatics 4.1. The content of non-aromatic $C_9$ hydrocarbons is 0.28% by weight including 0.06% by weight of n-nonane. The results of this Example show that the content of $C_9$ non-aromatic hydrocarbons, especially of n-nonane, is at the extreme of the tolerable limit for separation of the total xylenes by rectification. Furthermore, toluene and aromatic $C_9$–$C_{10}$ hydrocarbons are formed in an amount exceeding the amount thereof added to the fresh feedstock, i.e. a higher ratio between the recycle and feedstock is required. The Example illustrates the minimal content of H-mordenite in the catalyst.

EXAMPLE 7

As the feedstock use is made of a high-boiling fraction of the reforming catalysate as described in Example 1 hereinbefore.

The catalyst is employed consisting of the following components, percent by weight: Pt (platinum) 0.25; H-mordenite ($SiO_2/Al_2O_3=12$) 75; the balance being represented by alumina. The experiment is conducted at a temperature of from 480° to 490° C. under a pressure of 25 atm, circulation ratio of the hydrogen-containing gas of 1,200 nl/l of the feed and recycle (the content of hydrogen is 65% by volume), supply rate of fresh hydrogen of 200 nl/l of the feed and recycle.

The experiment is conducted with toluene recycle: 0.62 part by weight of fresh feedstock and 0.38 part by weight of toluene. At a space rate of the mixture of 2 $hr^{-1}$ the liquid product yield is 88.4% by weight including: benzene 11.3; toluene 38.0; xylenes 27.8; aromatic $C_9$–$C_{10}$ hydrocarbons 10.3; non-aromatic $C_9$–$C_{10}$ hydrocarbons 1.0. The content of $C_9$ non-aromatics in the liquid product is 0.15% by weight including 0.03% by weight of n-nonane.

EXAMPLE 8

Use is made of a catalyst containing, percent by weight: $MoO_3$ 5.0; Ni 1.0; H-Cl-mordenite 69; alumina 25. The content of Ce (cerium) in mordenite is 3.2% by weight which corresponds to the degree of substitution of hydrogen ions of about 22%. The high-boiling fraction of the reforming catalysate is employed, the fraction composition being the same as in Example 1 hereinbefore. Experiment with toluene recycle is conducted at a temperature of from 500° to 510° C. under a pressure of 35 atm, circulation ratio of the gas of 1,200 nl/l of the feed and recycle and the supply rate of fresh hydrogen of 200 nl/l of the feed and recycle. The content of hydrogen in the recycled gas is 60% by volume.

Proportions of the fresh feedstock and toluene are 0.65 and 0.35 part by weight respectively. At a space rate of the mixture of 1.5 $hr^{-1}$, the liquid product yield is 87.8% by weight including: benzene 12.1; toluene 35.0; xylenes 29.1; aromatic $C_9$–$C_{10}$ hydrocarbons 10.8; non-aromatic $C_5$–$C_9$ hydrocarbons 0.8. The content of n-nonane in the products is 0.03% by weight.

EXAMPLE 9

A catalyst is used containing, percent by weight: $MoO_3$ 5.0; $WO_3$ 0.5; H-Ca-mordenite 70; alumina 24.5. The content of Ca in mordenite is 1.44% by weight which is equivalent to the degree of substitution of hydrogen ions of about 16%. The feedstock of Example 1 is used. An experiment with recycle of toluene (0.35 part by weight of toluene and 0.65 part by weight of fresh feedstock) is conducted at a temperature of from 530° to 540° C. under a pressure of 50 atm, space rate of supply of the feed and recycle of 1.5 $hr^{-1}$; circulation ratio of the gas of 1,000 nl/l of the feed and recycle, fresh hydrogen supply rate of 200 nl/l of the feed and recycle. The content of hydrogen in the circulated gas is 60% by volume. The liquid product yield is 84.5% by weight including: benzene 12.8; toluene 35.0; total xylenes 27.2; aromatic $C_9$–$C_{10}$ hydrocarbons 8.8; non-aromatic $C_5$–$C_9$ hydrocarbons 0.7. The content of $C_9$-non-aromatics is 0.14% by weight, including 0.02% by weight of n-nonane.

What is claimed is:

1. A method of preparing benzene and xylenes from catalysates of reforming of gasoline fractions comprising a mixture of aromatic $C_6$–$C_{10}$ hydrocarbons and non-aromatic hydrocarbons comprising: separating a low-boiling fraction from said reforming catalysate by distillation at a temperature of from 90° to 108° C.; treating the remaining high-boiling fraction comprising toluene, $C_8$–$C_{10}$ aromatic hydrocarbons and paraffin hydrocarbons, in the presence of a hydrogen-containing gas at a temperature within the range of from 450° to 600° C. under a pressure of from 10 to 60 atm in contact with a catalyst consisting of 1 to 85% by weight of H-mordenite, 0.1 to 10% by weight of a hydrogenating component selected from the group consisting of:
 (a) oxides or sulfide of molybdenum;
 (b) oxides or sulfides of molybdenum combined with nickel;
 (c) oxides or sulfides of molybdenum combined with cobalt; and
 (d) platinum;
the balance being constituted by a binder, to produce a liquid aromatic hydrocarbon product; subjecting said liquid aromatic hydrocarbon product to rectification to produce benzene, toluene, total xylenes and $C_9$–$C_{10}$ aromatic hydrocarbons; separating p- and o-xylenes from the total xylenes; separating the benzene; recycling to the high-boiling fraction treatment a stream selected from the group consisting of toluene, toluene+aromatic $C_9$–$C_{10}$ hydrocarbons, and toluene+aromatic $C_9$–$C_{10}$ hydrocarbons+m-xylene.

2. A method as claimed in claim 1, wherein recycled to said stage of treatment of the high-boiling fraction is toluene along with aromatic $C_9$–$C_{10}$ hydrocarbons.

3. A method as claimed in claim 1, wherein recycled to said stage of treatment of the high-boiling fraction is toluene along with aromatic $C_9$–$C_{10}$ hydrocarbons and concentrate of m-xylene remaining after separation of o- and p-xylenes from total xylenes.

4. A method as claimed in claim 1, wherein the process is conducted at a space velocity of supply of the starting feed with the recycle to said stage of treatment of the high-boiling fraction within the range of from 1 to 8 volumes per one volume of the catalyst per hour, circulation ratio of the hydrogen-containing gas of from 600 to 2,000 nl/l of the liquid feed with the recycle and a content of hydrogen in the gas of at least 50% by volume.

5. A method as claimed in claim 1, wherein the recovered benzene is purified from impurities of non-aromatic hydrocarbons.

6. A method as claimed in claim 1, wherein the recovered benzene is mixed with the low-boiling fraction of the reforming catalysate and pure benzene is isolated from said mixture.

7. A method as claimed in claim 1, wherein n-mordenite contains alkali-earth and/or rare-earth metals in an amount equivalent to a degree of substitution of hydrogen in n-mordenite of up to 50%.

8. A method as claimed in claim 1, wherein as the binder use is made of alumina.

9. A method as claimed in claim 1, wherein the low-boiling fraction constitutes 20 to 35% by weight of the reforming catalysate.

10. A method as claimed in claim 1, wherein the high-boiling fraction comprises toluene, aromatic $C_8$–$C_9$ hydrocarbons, and paraffin hydrocarbons, wherein the amount of paraffin hydrocarbons in said high-boiling fraction is below 15% by weight.

11. A method as claimed in claim 1, wherein molybdenum is a catalyst component in the form of an oxide or sulphide.

12. A method as claimed in claim 1, wherein the recycled stream is primarily toluene.

13. A method as claimed in claim 1, wherein the recycled stream is primarily toluene and aromatic $C_9$–$C_{10}$ hydrocarbons.

14. A method as claimed in claim 1, wherein the recycled stream is primarily toluene, aromatic $C_9$–$C_{10}$ hydrocarbons and m-xylenes.

* * * * *